(12) United States Patent
Shikhman et al.

(10) Patent No.: US 8,012,165 B2
(45) Date of Patent: Sep. 6, 2011

(54) REMOVABLE SLEEVE

(75) Inventors: Oleg Shikhman, Trumbull, CT (US); Paul A. Scirica, Huntington, CT (US)

(73) Assignee: Interventional Therapies, Westport, CT (US)

( * ) Notice: Subject to any disclaimer, the term of this patent is extended or adjusted under 35 U.S.C. 154(b) by 0 days.

(21) Appl. No.: 10/277,794

(22) Filed: Oct. 22, 2002

(65) Prior Publication Data

US 2003/0109828 A1 Jun. 12, 2003

Related U.S. Application Data

(60) Provisional application No. 60/343,786, filed on Oct. 22, 2001.

(51) Int. Cl.
*A61B 17/32* (2006.01)
(52) U.S. Cl. ........................................ 606/170
(58) Field of Classification Search ................ 606/144, 606/148, 170, 174, 205–210, 167, 180, 184, 606/185, 139, 143, 213, 108, 103; 604/164.01, 604/264; 623/1.11, 1.12
See application file for complete search history.

(56) References Cited

U.S. PATENT DOCUMENTS

| | | | |
|---|---|---|---|
| 651,395 A | 6/1900 | Strapp | |
| 4,327,709 A | 5/1982 | Hanson et al. | 128/1 D |
| 4,444,184 A | 4/1984 | Oretorp | 128/305 |
| 4,491,132 A | 1/1985 | Aikins | 128/305 |
| 4,493,323 A | 1/1985 | Albright et al. | 128/340 |
| 4,557,255 A | 12/1985 | Goodman | 128/7 |
| 4,629,450 A | 12/1986 | Suzuki et al. | 604/164 |
| 4,723,545 A | 2/1988 | Nixon et al. | 128/305 |
| 4,744,364 A | 5/1988 | Kensey | 128/334 R |
| 4,760,840 A | 8/1988 | Fournier, Jr. et al. | 128/303.1 |
| 4,846,785 A | 7/1989 | Cassou et al. | 600/34 |
| 4,862,891 A | 9/1989 | Smith | 128/343 |
| 5,267,960 A * | 12/1993 | Hayman et al. | 604/106 |
| 5,318,589 A * | 6/1994 | Lichtman | 606/205 |
| 5,404,870 A | 4/1995 | Brinkerhoff et al. | |
| 5,545,170 A * | 8/1996 | Hart | 606/205 |
| 5,593,412 A * | 1/1997 | Martinez et al. | 623/1.11 |
| 5,613,974 A | 3/1997 | Andreas et al. | 606/144 |
| 5,630,833 A | 5/1997 | Katsaros et al. | 606/213 |
| 5,728,134 A | 3/1998 | Barak | |
| 5,810,849 A | 9/1998 | Kontos | |
| 5,830,125 A | 11/1998 | Scribner et al. | 606/139 |
| 5,855,585 A | 1/1999 | Kontos | |
| 5,860,991 A | 1/1999 | Klein et al. | 606/144 |
| 5,902,311 A | 5/1999 | Andreas et al. | 606/144 |
| 5,964,730 A * | 10/1999 | Williams et al. | 606/108 |
| 5,967,997 A * | 10/1999 | Turturro et al. | 600/170 |
| 5,989,276 A | 11/1999 | Houser et al. | |
| 6,039,748 A * | 3/2000 | Savage et al. | 606/184 |

(Continued)

FOREIGN PATENT DOCUMENTS

SU 1623627 A1 4/1988

(Continued)

*Primary Examiner* — Kevin T Truong
(74) *Attorney, Agent, or Firm* — Cantor Colburn LLP

(57) ABSTRACT

A removable sleeve is provided, which comprises a shaft portion configured to engage at least a portion of a percutaneous device. The shaft portion may be substantially fitted to the external dimensions of a percutaneous device. The removable sleeve also comprises a handle portion at a proximal end of the shaft portion. The handle portion is positioned such that upon proper introduction of the percutaneous device, the shaft portion may easily be moved proximally to expose an operative region of the percutaneous device.

12 Claims, 4 Drawing Sheets

U.S. PATENT DOCUMENTS

| | | | |
|---|---|---|---|
| 6,090,130 A | 7/2000 | Nash et al. | 606/213 |
| 6,102,920 A | 8/2000 | Sullivan et al. | |
| 6,106,532 A | 8/2000 | Koike et al. | |
| 6,110,184 A | 8/2000 | Weadock | 606/144 |
| 6,132,440 A | 10/2000 | Hathaway et al. | |
| 6,143,004 A | 11/2000 | Davis et al. | |
| D436,663 S | 1/2001 | Chandler et al. | |
| D437,413 S | 2/2001 | Chandler et al. | |
| 6,221,084 B1 | 4/2001 | Fleenor | |
| 6,277,140 B2 | 8/2001 | Ginn et al. | |
| 6,287,322 B1 * | 9/2001 | Zhu et al. | 606/213 |
| 6,355,050 B1 | 3/2002 | Andreas et al. | 606/144 |
| 6,440,154 B2 | 8/2002 | Gellman et al. | |
| 6,454,777 B1 | 9/2002 | Green | |
| 6,551,330 B1 | 4/2003 | Bain et al. | |
| 6,551,331 B2 | 4/2003 | Nobles et al. | |
| 7,052,500 B2 * | 5/2006 | Bashiri et al. | 606/113 |
| 2002/0082614 A1 | 6/2002 | Logan et al. | |
| 2002/0082617 A1 | 6/2002 | Nishtala et al. | |
| 2002/0087169 A1 | 7/2002 | Brock et al. | |
| 2002/0087178 A1 | 7/2002 | Nobles et al. | |
| 2002/0193808 A1 | 12/2002 | Belef et al. | |

FOREIGN PATENT DOCUMENTS

| | | |
|---|---|---|
| WO | W09301755 | 2/1993 |
| WO | WO0135833 | 5/2001 |
| WO | WO0167966 | 9/2001 |

* cited by examiner

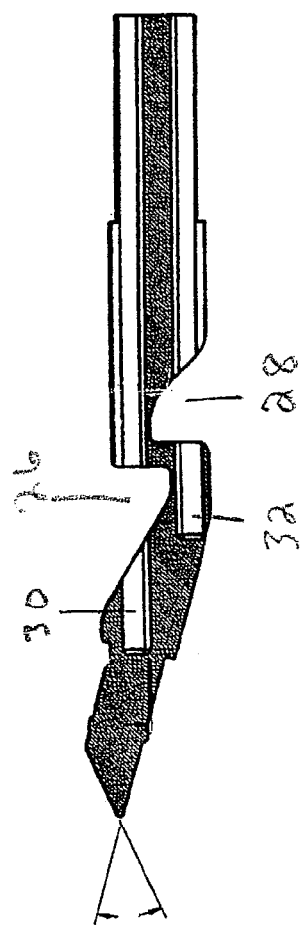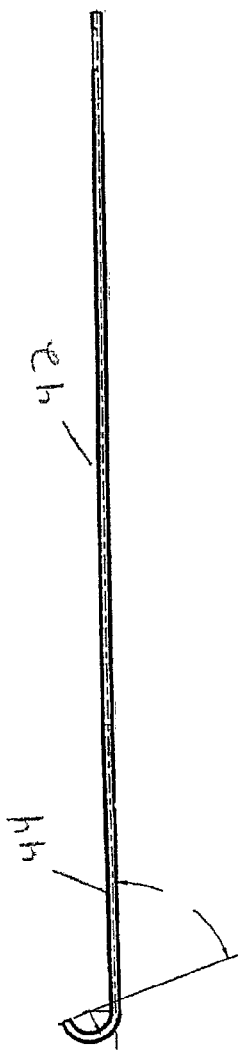

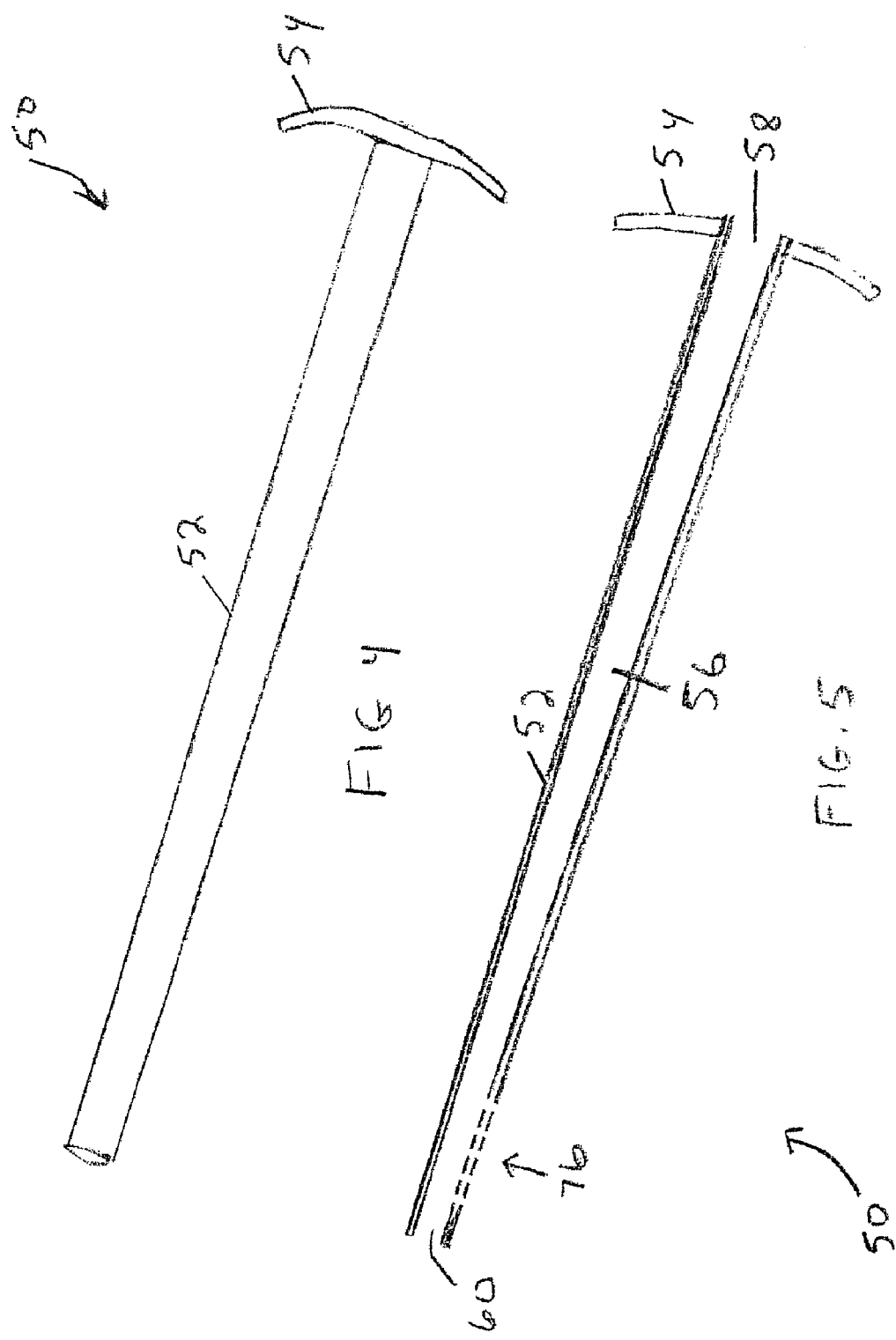

REMOVABLE SLEEVE

CROSS-REFERENCE TO RELATED APPLICATIONS

The present application claims priority to U.S. Provisional Patent Application Ser. No. 60/343,786, entitled Removable Sleeve, filed Oct. 22, 2001 and assigned to the common assignee hereof, the entire contents of which are incorporated by reference herein in its entirety.

BACKGROUND

When performing catheterization procedures, such an angiography or angioplasty, a catheter is generally introduced percutaneously (i.e., through the skin) into the vascular system by first penetrating the skin and underlying tissue, and then the blood vessel, with a sharpened hollow needle. Location of a blood vessel, such as an artery, is typically achieved by feeling for the pulse, since such structures usually cannot be seen through the skin. Next, a guide wire is commonly inserted through the lumen of the hollow needle and is caused to enter the selected blood vessel. Subsequently, the needle is typically slid off the guide wire and a combination of a dilator and sheath are fed over the guide wire and pushed through the skin to enter the vessel. The guide wire and dilator can then be removed and the desired catheter to carry out the procedure is fed through the lumen of the sheath and advanced through the vascular system until the working end of the catheter is appropriately positioned. Following the conclusion of the catheterization procedure, the working catheter will be withdrawn and, subsequently, the sheath can also be removed from the wound, or left in place to facilitate closure.

At this point in the procedure, the vessel leakage is controlled in order to stem the flow of blood through the puncture. Because it is common practice to administer a blood thinning agent to the patient prior to many of the catheterization procedures, stemming the blood flow can be troublesome. A common method of sealing the wound is to maintain external pressure over the vessel until the puncture naturally seals. This method of puncture closure typically takes at least thirty minutes, with the length of time usually being substantially greater if the patient is hypertensive or anti-coagulated. In some anti-coagulated patients, the sheath is left in place for hours to allow the anti-coagulant to wear off. When human hand pressure is utilized, it can be uncomfortable for the patient and can use costly professional time on the part of the hospital staff. Other pressure techniques, such as pressure bandages, sandbags or clamps, have been employed, but these devices also require the patient to remain motionless for an extended period of time and the patient must be closely monitored to ensure their effectiveness.

An alternative method for wound closure includes the use of a percutaneous suturing device, such as is described by co-pending U.S. Provisional Patent Application Ser. No. 60/343,786, entitled Vascular Suturing Device, filed Oct. 22, 2001 and assigned to the common assignee hereof and incorporated by reference herein in its entirety. The percutaneous suturing device described by that application is a device for closure of a wound in a patient, such as a puncture hole in a blood vessel. The apparatus, illustrated generally at 10 in FIG. 1, includes a housing, shown generally at 12, a shaft 14 having first 16 and second 18 ends in which the first end 16 is coupled to the housing 12, a tissue engaging section 20 coupled to the second end 18 of the shaft 14, and first 22 and second 24 needles which extend from the housing 12 through the shaft 14 into the tissue engaging section 20. The tissue engaging section 20 is directed through the wound, and has first 26 and second 28 gaps (best seen in FIG. 2) in which each gap has opposing surfaces into which different sides of the wound can be received. The first needle 22 is extendable into a holder 30 through the first gap 26 to capture one of the two ends of a suture material or thread (not shown), and is retractable with the captured suture. The second needle 24 is extendable into another holder 32 through the second gap 28 to capture the opposite end of the suture material (not shown), and is retractable with the captured suture. A selecting mechanism 34 (FIG. 1) determines which of the first or second needles 22, 24 are can be driven. The user operates an actuator member 36 to drive and retract each of the selected needles to retrieve each end of the suture material through the tissue about the wound. The actuator member is biased into an extended position (non-needle driving position) by springs 38, 40. A flexible distal member 42 is shown extending distally from the tissue engaging section 20. The flexible distal member 42 (FIGS. 1 and 3) may include a channel 44 extending through at least a portion of the member for receipt of a guide wire (not shown).

Percutaneous devices, such as the suturing device described in the above-referenced co-pending application, as well as other devices not specifically enumerated, are generally introduced percutaneously through introducer sheaths, which must first be inserted into a vessel dilated to the size of the introducer sheath. The introducer sheaths have significantly larger diameters than the tool to be introduced into the vessel to facilitate introduction and removal of the device there from. For example, a 6 French device may require a 9 French or larger introducer at the wound site.

There remains a need in the art for more effective and efficient methods of introducing percutaneous devices.

SUMMARY

The above described and other problems and disadvantages in the field of percutaneous device introducers are overcome and alleviated by the present removable sleeve, which comprises a shaft portion configured to engage at least a portion of the percutaneous device. In another embodiment, the shaft portion is substantially fitted to the external dimensions of the operative section of a percutaneous device, and a handle portion is provided at a portion of the shaft proximal to the operative section, the handle portion facilitating proximal movement of the shaft over the percutaneous device.

In one embodiment, the shaft portion is a flexible material that is configured to engage at least a portion of the percutaneous device. In another embodiment, the shaft portion is substantially form fitted to an operative region of the percutaneous device and that extends proximally to a handle portion. The handle portion facilitates proximal movement of the shaft portion once the operative portion of the percutaneous device is properly positioned. Because, in this embodiment, the shaft portion comprises a flexible material, the distal regions of the shaft portion will permit proximal movement of the shaft region, even where the percutaneous device has a greater diameter at points proximal to the operative portion (i.e., allowing the removable sleeve to expand as it is pulled proximally over the percutaneous device).

In another embodiment, the shaft portion comprises a relatively inflexible material that will maintain integrity during introduction of the percutaneous device, but will rupture or split upon proximal movement of the shaft portion over a percutaneous device with increasing diameters proximal to an operative portion.

In another embodiment, the shaft portion is provided with at least one serration for facilitating rupture or split upon proximal movement of the shaft portion over a percutaneous device with increasing diameters proximal to an operative portion.

The above described and other features are exemplified by the following FIGURES and detailed description.

BRIEF DESCRIPTION OF THE DRAWINGS

Referring now to the various FIGURES, wherein like elements are numbered alike:

FIG. 2 is a cross sectional view of the tissue engaging section of the exemplary percutaneous suturing apparatus;

FIG. 3 is a cross sectional view of the flexible distal member of the exemplary percutaneous suturing apparatus;

FIG. 4 is a perspective view of an exemplary removable sleeve;

FIG. 5 is a cross sectional view of an exemplary removable sleeve; and

DETAILED DESCRIPTION

Figure 1:
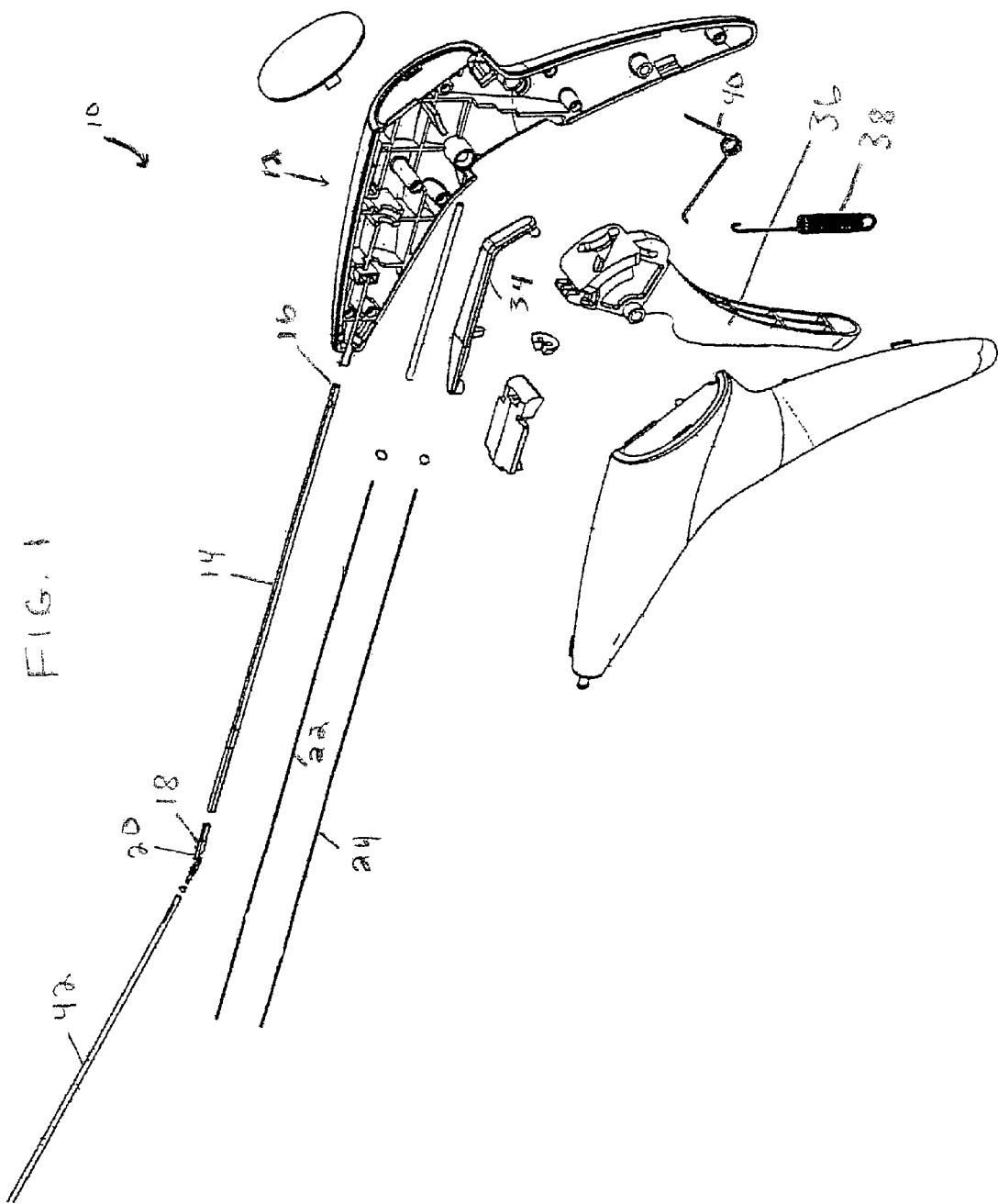
FIG. 1 is a perspective view of an exemplary percutaneous suturing apparatus.

Referring now to FIGS. 4-5, perspective and cross sectional views of an embodiment of the present removable sleeve are illustrated generally at 50. The removable sleeve 50 generally comprises a shaft portion 52 and a handle portion 54. An interior of the shaft portion 52 defines a lumen 56, having proximal 58 and distal 60 openings. In one exemplary embodiment, the handle portion 54 extends away from the shaft portion 52 and is sufficiently rigid to permit a user to manipulate the removable sleeve 50 in a proximal direction.

Figure 6:
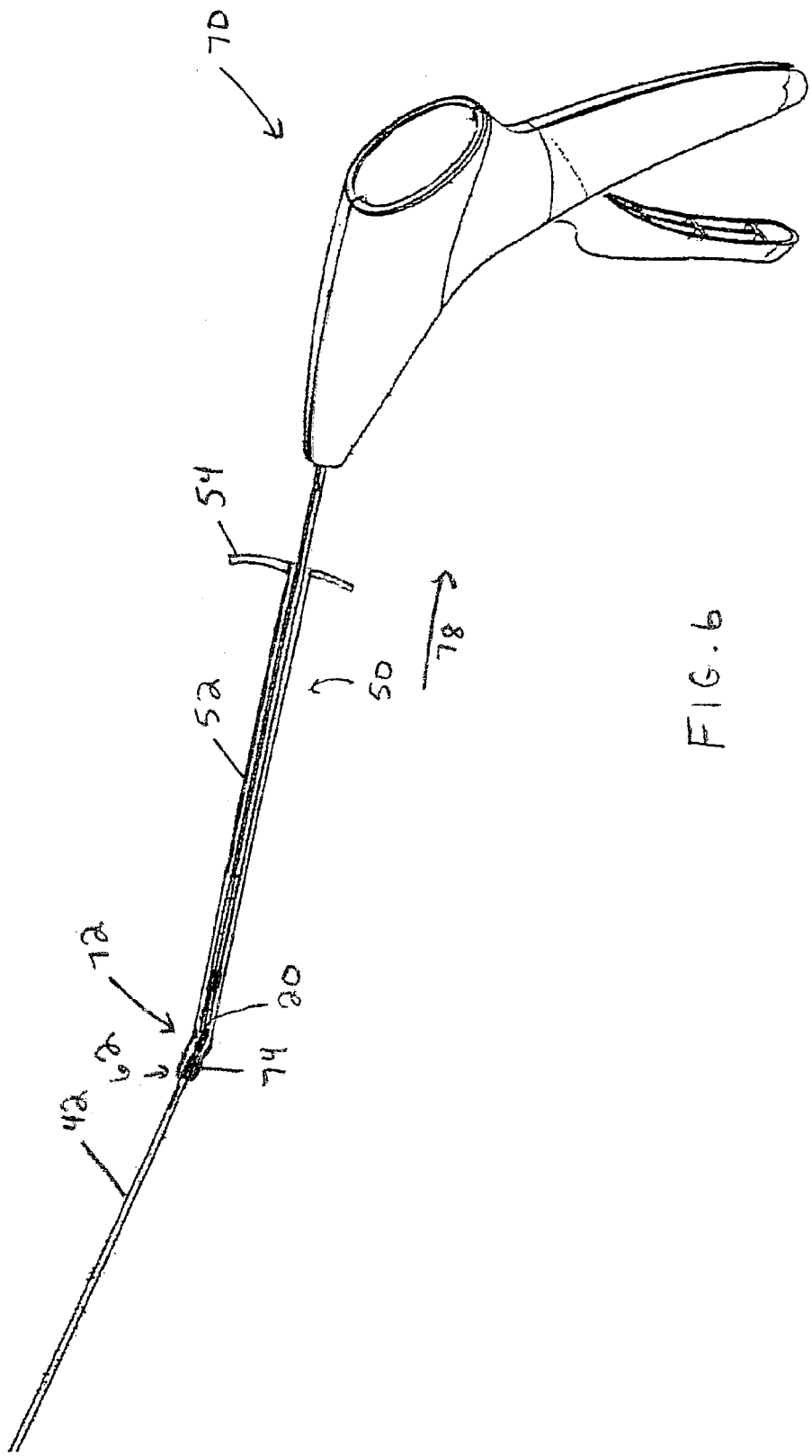
FIG. 6 is a cross sectional view of an exemplary removable sleeve in position over an exemplary percutaneous suturing device.

With reference to FIG. 6, at least a portion (exemplified generally at 62) of the shaft portion 52 is configured to engage the external dimensions of a percutaneous device, shown generally at 70. In one embodiment, the shaft portion 52 comprises, at least in part, a flexible material that is substantially fitted to an operative region (shown generally at 72) of the percutaneous device. The shaft portion 52 extends proximally to handle portion 54. The handle portion 54 facilitates proximal movement of the shaft portion 52 once the operative portion 72 of the percutaneous device 70 is properly positioned. Because, in this exemplary embodiment, the shaft portion 52 comprises a flexible material, the distal regions 74 of the shaft portion 52 will permit proximal movement of the shaft portion 52, even when the percutaneous device 70 has greater diameters at points proximal to the operative portion 72. Thus, areas of the shaft portion 52 may expand as the removable sleeve 50 is pulled proximally over the percutaneous device.

In another embodiment, the shaft portion 52 comprises a relatively inflexible material that is substantially form fitted to at least a portion of the percutaneous device 70 and that will maintain integrity during introduction of the percutaneous device 70, but will rupture or split upon proximal movement of the shaft portion 52 over a percutaneous device 70 with increasing diameters proximal to an operative portion.

In another embodiment, the shaft portion 52 is provided with at least one serration (shown generally at 76 in FIG. 5) for facilitating rupture or split upon proximal movement of the shaft portion 52 over a percutaneous device 70 with increasing diameters proximal to an operative portion.

In another embodiment, a distal end portion 74 of the shaft portion 52 is form fitted to the flexible distal member 42 of a percutaneous suturing device 70. The shaft portion 52 covers the tissue engaging section 20 and extends proximally to a handle portion 54. The handle portion 54 is positioned such that upon proper introduction of the suturing device, the shaft portion may be moved proximally along the line 78 to expose the tissue engaging section 20 of the percutaneous suturing device 70.

As referenced above, the shaft portion of the present removable sleeve may comprise relatively rigid or flexible materials, or combinations of rigid and flexible materials. Suitable materials may include, but are not limited to, polymeric materials, including polyethylene, among others. The shaft portion removable sleeve may be constructed of a shrinkable plastic, including without limitation, shrink tubing or shrink wrap, that will form to the desired shape and diameter, or it may be cut or molded to the desired shape and diameter and threaded over the percutaneous device prior to introduction of that device. In one embodiment, the shaft portion is a shrink wrap material that is heated or cured to size over the percutaneous device. In another embodiment, the shaft portion comprises a material that averages above about 0.001 inch in wall thickness. In another embodiment, the shaft portion comprises a material that averages below about 0.003 inch in wall thickness. In another embodiment, the shaft portion has external dimensions at a distal end portion that is between about 6 and 8 French in size. In another embodiment, the shaft portion has external dimensions at a distal end portion that are about 7 French in size.

The handle portion of the present removable sleeve may be formed integral with the shaft portion, or it may be attached to the shaft portion, including without limitation, by fusing or gluing.

The shaft portion of the present removable sleeve may be configured to operate with any number of percutaneous devices, including without limitation, catheters of all sorts, suturing devices of all sorts and obturators.

The present removable sleeve advantageously allows introduction of a percutaneous device without the need for separate, bulky introducer sheaths and dilators. The device is configured to maintain integrity over an operative region of the percutaneous device during insertion of the percutaneous device into an operative position while minimizing dilation of the wound prior to operation. The device is easily retracted proximally to expose an operative region of the percutaneous device.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore it is intended that the invention not be limited to the particular embodiments disclosed as the best modes above.

What is claimed is:

1. A percutaneous surgical suturing device including a removable sleeve, the removable sleeve comprising a shaft portion configured to engage at least a portion of the percutaneous device, the shaft portion covering an operative section of the percutaneous device in a first position, the operative section of the percutaneous device comprising at least one tissue engaging suturing gap, the shaft configured to exert a bias-against at least a portion of the percutaneous device when said shaft is in said first position or when said shaft is urged in a proximal direction relative to said device, the shaft slideable in a proximal direction to overcome the action of at least a portion of said bias to expose said at least one tissue suturing gap of said percutaneous device.

2. The percutaneous surgical suturing device of claim 1, further comprising a handle positioned on a proximal portion of said shaft, the handle positioned such that subsequent to introduction of the percutaneous device, the shaft portion may be moved proximally to expose the tissue engaging section of the suturing device.

3. The percutaneous surgical suturing device of claim 2, wherein said handle includes at least one member projecting approximately in a perpendicular direction relative to said shaft, the member of sufficient length to allow a user to use at least one finger to pull the handle and attached shaft proximally over the percutaneous device.

4. The percutaneous surgical suturing device of claim 3, wherein said handle includes two members projecting approximately in perpendicular directions relative to said shaft, the two members projecting in approximately opposite directions to permit the user to grasp the handle on approximately opposite sides of said shaft to pull the handle and attached shaft proximally over the percutaneous device.

5. The percutaneous surgical suturing device of claim 1, wherein at least a portion of said shaft is a polymeric material.

6. The percutaneous surgical suturing device of claim 1, wherein at least a portion of said shaft comprises a polyethylene material.

7. The percutaneous surgical suturing device of claim 1, wherein at least a portion of said shaft is constructed of a shrinkable plastic.

8. The percutaneous surgical suturing device of claim 7, wherein said shaft portion is a shrink wrap material that is heated or cured to size over the percutaneous device.

9. The percutaneous surgical suturing device of claim 1, wherein at least a portion of said shaft comprises a material that averages between about 0.001 inch in wall thickness and below about 0.003 inch in wall thickness.

10. The percutaneous surgical suturing device of claim 1, wherein said shaft has external dimensions at a distal end portion that is between about 6 and 8 French in size.

11. The percutaneous surgical suturing device of claim 1, wherein said shaft has external dimensions at a distal end portion that is equal to or below about 7 French in size.

12. The percutaneous surgical suturing device of claim 1, wherein the shaft portion is provided with at least one serration for facilitating rupture or split upon proximal movement of the shaft portion over a percutaneous device with increasing diameters proximal to an operative portion.

* * * * *